July 31, 1956 R. L. BYRUM Plant Pat. 1,504
ROSE PLANT
Filed Oct. 10, 1955
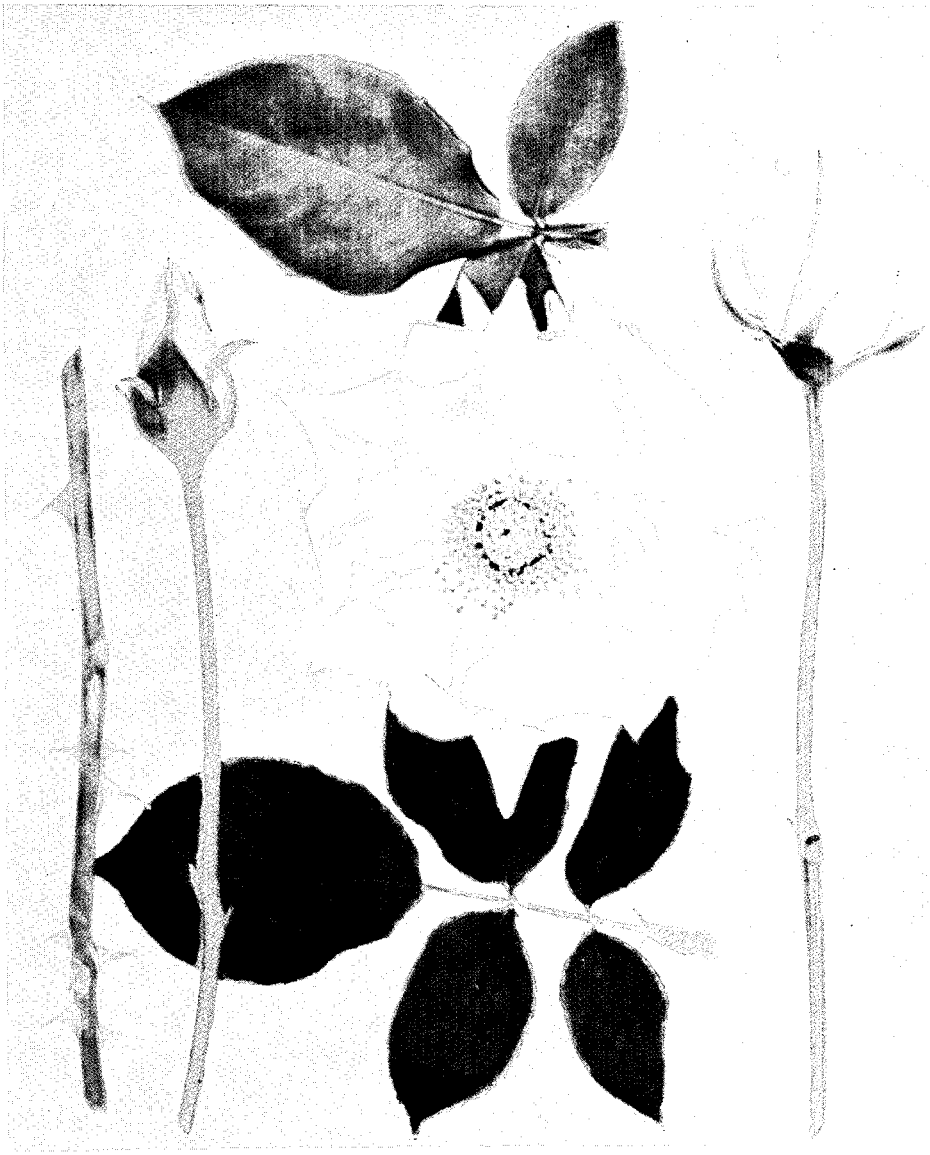
Inventor
R. L. Byrum
By: Robb & Robb
Attorneys.

United States Patent Office

Plant Pat. 1,504
Patented July 31, 1956

1,504

ROSE PLANT

Roy L. Byrum, Richmond, Ind., assignor to Joseph H. Hill Company, Richmond, Ind., a corporation of Indiana Application October 10, 1955, Serial No. 539,708

1 Claim. (Cl. 47—61)

The present invention relates to a new and distinct variety of rose plant of the hybrid tea class, which was originated by me by crossing an unnamed and unpatented seedling identified in the breeding records of my employer-assignee as #40/43, with the variety "Orange Delight," known in Europe as "Queen Juliana" (Plant Patent No. 874).

The primary objective in making this cross was to produce a new rose variety, the blooms of which have the distinctive and attractive color of those of the variety "Orange Delight," the good bud formation of both parent varieties, and the good petal texture and bloom size corresponding to those of the unnamed seedling parent. This objective was fully achieved, along with other improvements in the new variety.

The outstanding features of novelty and distinctiveness of my new variety are as follows:

(1) Its prolific blooming habit;
(2) Its good winter-forcing characteristics;
(3) Its good bud formation and bloom size;
(4) The slow-opening habit of its blooms;
(5) The good petal texture of its blooms; and
(6) The distinctive and attractive color of its blooms corresponding to that of the parent variety "Orange Delight."

In comparison with its parent varieties, the new variety is a better winter-forcer and is more productive than either parent.

The foregoing features definitely differentiate my new variety from its parents, as well as from all other varieties of its class of which I am aware, and asexual reproduction of the new variety by budding as performed in Texas, and by grafting as performed at Richmond, Indiana, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Koster's Color Guide (hereinafter abbreviated as "Koster"), as indicated:

Type: Greenhouse; bush; seedling.
Class: Hybrid tea.
Breeding: Seedling.
*Seed parent.*—An unnamed seedling identified as #40/43.
*Pollen parent.*—"Orange Delight" (known in Europe as "Queen Juliana").
Propagation: Holds its distinguishing characteristics through succeeding propagations by both budding and grafting.

FLOWER

Locality where grown and observed: Richmond, Indiana.
Flowers borne: 1 to stem; on strong stems of medium length.
Quantity of bloom: Abundant, in greenhouse.
Continuity: Continuous.
Fragrance: Slight. Nature—tea.
Bud:
*Peduncle.*—Medium length; medium diameter; strong; erect. Bark—smooth. Color—Scheele's Green, Plate 860/2 (Wilson). Thorns—none. Prickles—none. Hairs—none.
*Before calyx breaks.*—Size—medium small. Form—short pointed; with a conspicuous neck; with foliaceous appendages on the surface of the bud; with slender foliaceous parts extending beyond the tip of the bud equal to ¼ or more of its length. Color—Scheele's Green, Plate 860 (Wilson).
*As calyx breaks.*—Color (outside of petal)—Nasturtium Orange, Plate 610/1 (Wilson).
*As first petal opens.*—Size—medium large. Form—short pointed. Color: Outside—Saffron Yellow, Plate 7/1 (Wilson), with base of petal Aureolin, Plate 3/1 (Wilson); inside—Saffron Yellow, Plate 7 (Wilson), some with a stripe of Buttercup Yellow, Plate 5/3 (Wilson) running lengthwise through center.
*Opening.*—Opens up well in greenhouse; affected normally by weather conditions, but with no unusual characteristics.
Bloom:
*Size (when fully open).*—Medium large; from 3 inches to 4 inches.
*Petalage.*—Double (more petals, but the stamens not hidden); from 30 to 35 petals; arranged regularly.
*Form.*—Full and high-centered at first, but becoming open; petals being at first very tightly rolled outward, but becoming loosely rolled outward later at maturity.
Petals:
*Texture.*—Thick; leathery; with both inside and outside satiny.
*Shape.*—Outside petals—obovate, with apex obtuse; one petal occasionally having 1 notch. Intermediate petals—obovate, with apex obtuse; no notches. Inside petals—obovate, with apex obtuse; no notches.

This description of a newly opened flower was made from a rose grown in a greenhouse in the month of March, at Richmond, Indiana:

*Color.*—Outer petal: outside surface—between Maize Yellow, Plate 607 (Wilson) and Maize Yellow, Plate 607/1 (Wilson), with base of petal Aureolin, Plate 3/1 (Wilson); inside surface—between Buttercup Yellow, Plate 5/1 (Wilson) and Buttercup Yellow, Plate 5/2 (Wilson). Intermediate petal: Outside surface—between Maize Yellow, Plate 607 (Wilson) and Maize Yellow, Plate 607/1 (Wilson), with base of petal Auerolin, Plate 3/1 (Wilson); inside surface—between Buttercup Yellow, Plate 5/1 (Wilson) and Buttercup Yellow, Plate 5/2 (Wilson). Inner petal: Outside surface—between Maize Yellow, Plate 607 (Wilson) and Maize Yellow, Plate 607/1 (Wilson), with base of petal Aureolin, Plate 3/1 (Wilson); inside surface—between Buttercup Yellow, Plate 5/1 (Wilson) and Buttercup Yellow, Plate 5/2 (Wilson.)

This description was made from a rose that was open for 3 days in a greenhouse in the month of March, at Richmond, Indiana:

*Color.*—Outer petal: Outside surface—shading from Egyptian Buff, Plate 407/3 (Wilson) through Egyptian Buff, Plate 407/2 (Wilson), with base of petal Sulphur Yellow, Plate 1/2 (Wilson); inside surface—shading from Buttercup Yellow, Plate 5/3 (Wilson) through Buttercup Yellow, Plate 5/2 (Wilson), with base of petal Sulphur Yellow, Plate 1/2 (Wilson). Intermediate petal: Outside surface—shading from Egyptian Buff, Plate 407/3 (Wilson) through Egyptian Buff, Plate 407/2 (Wilson), with base of petal Sulphur Yellow, Plate 1/2 (Wilson); inside surface—shading from Buttercup Yellow, Plate 5/3 (Wilson) through Buttercup Yellow, Plate 5/2 (Wilson), with base of petal Sulphur Yellow, Plate 1/2 (Wilson). Inner petal: Outside surface—shading from Egyptian Buff, Plate 407/3 (Wilson) through Egyptian Buff, Plate 407/2 (Wilson), with base of petal Sulphur Yellow, Plate 1/2 (Wilson); inside surface—shading from Buttercup Yellow, Plate 5/3 (Wilson) through Buttercup Yellow, Plate 5/2 (Wilson), with base of petal Sulphur Yellow, Plate 1/2 (Wilson).

*General color effect of open bloom.*—Newly opened flower—Shading from Maize Yellow, Plate 607 (Wilson) through Maize Yellow, Plate 607/1 (Wilson) to Maize Yellow, Plate 607/2 (Wilson). 3 days-open—Amber Yellow, Plate 505/1 (Wilson).

*Behavior of petals.*—Persist, in greenhouse; normally affected by weather conditions, but with no unusual characteristics; fading to Egyptian Buff, Plate 407/3 (Wilson).

*Flower longevity.*—Cut roses grown in greenhouse and kept at living-room temperatures—5 or 6 days in March.

REPRODUCTIVE ORGANS

Stamens: Many; arranged regularly about pistils.

Filaments: Long; most with anthers. Color—Indian Yellow, Plate 6 (Wilson).

Anthers: Medium large; all open at once. Color—Yellow Ochre, Plate 07 (Wilson).

Pollen: Abundant. Color—Yellow Ochre, Plate 07 (Wilson).

Pistils: Many.

Styles: Uneven; short; medium heavy; bunched. Color—Crimson, Plate 22/1 (Wilson).

Stigma: Color—Pure White, Plate #1 (Koster).

Ovularies: Most encased in calyx, but few protruding from calyx.

Hips: None.

Sepals: Permanent; medium length; straight; slightly curled. Color: Inside—Pod Green, Plate 061/2 (Wilson), overlaid with White fuzz; Outside—Scheele's Green, Plate 860/3 (Wilson), overlaid with Scheele's Green, Plate 860 (Wilson).

Seeds: None.

PLANT

Foliage:

*Leaves.*—Compound of 5 to 7 leaflets; abundant; medium large; heavy; leathery.

*Leaflets.* — Shape — oblong. Apex — mucronate. Base—round. Margin—simply serrate.

*Color.*—Mature: Upper surface—near Spinach Green, Plate 0960 (Wilson), but darker; under surface—near Cedar Green, Plate #80 (Koster). Young: Upper surface—near Scheele's Green, Plate 860/3 (Wilson), slightly overlaid with Magenta, Plate #50 (Koster), with edge of leaves Magenta, Plate #50 (Koster); under surface—near Pod Green, Plate 061/2 (Wilson), overlaid with Magenta, Plate #50 (Koster).

*Rachis (the supporting stem of the compound leaf).*—Medium heavy. Upper side—grooved. Under side—smooth.

*Stipules.*—Moderately long; very narrow; with very short points turning out at an angle of more than 45°.

Growth:

*Habit.*—Bush; upright; much-branched.

*Growth.*—Free; vigorous.

*Canes.*—Medium diameter.

*Main stems.*—Color—some Spinach Green, Plate 0960/2 (Wilson); some Spinach Green, Plate 0960/2 (Wilson), overlaid with streaks of Van Dyck Brown, Plate #96 (Koster). Thorns—several; medium length; hooked downward; with long base. Color—Van Dyck Brown, Plate #96 (Koster). Prickles—none. Hairs—none.

*Branches.*—Color—Scheele's Green, Plate 860 (Wilson). Thorns—several; long; hooked downward; with long base. Color—Sap Green, plate 62/2 (Wilson), overlaid with Violet Rose, Plate #39 (Koster) at base of thorn. Prickles—none. Hairs—none.

*New shoots.*—Color—shading from Lettuce Green, Plate 861/2 (Wilson) through Lettuce Green, Plate 861/1 (Wilson) at base. Thorns—several; medium length; hooked downward; with long base. Color—near French Purple, Plate #42 (Koster) at base, gradually shading to Sap Green, Plate 62/3 (Wilson) at tip. Prickles—none. Hairs—none.

I claim:

A new and distinct variety of rose plant of the hybrid tea class, substantially as herein shown and described, characterized particularly as to novelty by its very prolific blooming habit, its good winter-forcing characteristics, its good bud formation and bloom size, the slow-opening habit of its blooms, the good texture of its flower petals, and its distinctive bloom color corresponding to that of the variety "Orange Delight" (Plant Patent No. 874).

No references cited.

Dedication

Plant Pat. No. 1,504.—*Roy L. Byrum*, Richmond, Ind. ROSE PLANT. Patent dated July 31, 1956. Dedication filed Sept. 21, 1971, by the assignee, *Joseph H. Hill Company*.

Hereby dedicates its entire interest in the said patent to the Public of the United States.

[*Official Gazette November 9, 1971.*]